United States Patent

Goldman

[11] Patent Number: 5,451,725
[45] Date of Patent: Sep. 19, 1995

[54] HOLDER FOR A STETHOSCOPE OR THE LIKE

[76] Inventor: Julian M. Goldman, 130 S. Hudson St., Denver, Colo. 80222-1165

[21] Appl. No.: 273,752

[22] Filed: Jul. 12, 1994

[51] Int. Cl.[6] .............................. A61B 7/02; A45F 5/00
[52] U.S. Cl. ..................................... 181/131; 224/269; 24/306
[58] Field of Search ................. 181/131; 224/901, 250, 224/269; 24/306, 442

[56] References Cited

U.S. PATENT DOCUMENTS

| | | | |
|---|---|---|---|
| 742,790 | 10/1903 | Jones | 181/131 |
| 1,268,075 | 5/1918 | Glynn | 24/306 |
| 2,669,231 | 2/1954 | Fisher . | |
| 3,374,508 | 3/1968 | Slimovitz | 24/306 |
| 4,291,439 | 9/1981 | Riti | 24/306 |
| 4,308,642 | 1/1982 | Heyman | 24/306 |
| 4,571,245 | 2/1986 | Hubbard et al. . | |
| 4,639,980 | 2/1987 | Peterson | 24/306 |
| 4,700,432 | 10/1987 | Fennell . | |
| 4,815,172 | 3/1989 | Ward | 24/442 |
| 4,879,787 | 11/1989 | Walls | 24/306 |
| 4,969,239 | 11/1990 | Bruno | 24/306 |
| 5,098,399 | 3/1992 | Tollini . | |
| 5,172,683 | 12/1992 | West | 224/901 X |

Primary Examiner—Khanh Dang
Attorney, Agent, or Firm—Burns, Doane, Swecker & Mathis

[57] ABSTRACT

A monaural stethoscope attached to a holder having a hook and loop fastening system. The holder is configured such that when the loop fastening material is folded up on itself, it mates with the hook fastening material to form a closed loop for retaining the coiled tubing of the monaural stethoscope. A pin fastener, such as a safety pin, is attached to the back of the holder so that the holder can be pinned to a medical garment, such as an anesthesiologist's scrub suit.

11 Claims, 2 Drawing Sheets

HOLDER FOR A STETHOSCOPE OR THE LIKE

BACKGROUND OF THE INVENTION

1. Field of the Invention

The present invention is directed to a holder for a stethoscope or other articles for medical personnel, more particularly, to a novel and improved type of holder for a monaural stethoscope which can be attached to a medical garment and used to retain the substantial length of tubing associated with the monaural stethoscope.

2. Prior Art

A monaural stethoscope is a device used routinely by an anesthesiologist to monitor a patient during the administration of anesthesia. The monaural stethoscope consists of a long piece of tubing (usually 3 to 5 feet long) with a molded ear piece on one end that fits in the anesthesiologist's ear and a connector on the other end that attaches to a patient's precordial or esophageal stethoscope. Following the completion of administering anesthesia or during administration, the monaural stethoscope may be disconnected from the patient's stethoscope so that the anesthesiologist may move about freely in the operating room or to another patient. The monaural stethoscope may then be reconnected to the same patient or connected to another patient.

One of the limitations of the monaural stethoscope is that the 3 to 5 feet of tubing is cumbersome to accommodate when the anesthesiologist moves to another patient. Anesthesiologists have attempted different methods to solve this problem. Some of them wrap the tubing around their necks and tuck the free end into their scrub shirt. Others coil the tubing up and place it in their scrub shirt pocket. Still others coil the tubing up and place it in their scrub pants. All of these methods have their own limitations ranging from unsanitary to cumbersome.

Another of the limitations of the monaural stethoscope is that the earpiece is easily pulled from the anesthesiologist's ear if the anesthesiologist inadvertently moves away from the patient before disconnecting the stethoscope from the patient's stethoscope or if someone bumps into the tubing when the monaural stethoscope is attached to the patient's stethoscope. Either of these events can be painful and/or damage the monaural stethoscope.

In view of the limitations of prior attempts to accommodate the substantial length of tubing of the monaural stethoscope, it would be highly desirable to have a holder that would retain the stethoscope in a convenient location when the stethoscope is not being used and that would help prevent the earpiece from being pulled from the anesthesiologist's ear inadvertently when the stethoscope is being used. It would also be desirable to have a device for holding articles, such as rings, watches, key rings, etc. in a secure fashion for medical personnel.

SUMMARY OF THE INVENTION

One purpose of the subject invention is to provide a holder for a monaural stethoscope that can be attached to a medical garment and which retains the substantial length of tubing associated with the monaural stethoscope in a convenient location when the stethoscope is not being used. Another purpose of the present invention is to prevent the earpiece of the monaural stethoscope from being pulled accidentally from the anesthesiologist's ear.

To accomplish these purposes there is provided a monaural stethoscope attached to a holder having a hook and loop fastening system. The holder is configured such that when the loop fastening material is folded up on itself, it mates with the hook fastening material to form a closed loop for retaining the tubing of the monaural stethoscope in a coiled fashion. A pin fastener, such as a safety pin, is attached to the back of the holder so that the holder can be pinned to a medical garment, such as an anesthesiologist's scrub suit.

In one aspect of the invention there is provided a medical device, comprising a holding strap having a loop securing surface along its length thereof and a first end, a patch having a hook securing surface, the patch being attached to the first end of the holding strap so that when the holding strap is folded over on itself the loop securing surface and hook securing surface mate to form a closed loop, a pin fastener pivotally journalled in the first end of the holding strap for removably securing the holder to a garment, and an aural stethoscope attached to the medical device so that the aural stethoscope can be coiled up and placed in the closed loop created when the holding strap is folded over on itself.

In another aspect of the invention there is provided a holder for an aural stethoscope or the like, comprising a holding strap having a loop securing surface along its length thereof and a first end, a patch having a hook securing surface, the patch being attached to the first end of the holding strap so that when the holding strap is folded over on itself the loop securing surface and hook securing surface mate to form a closed loop, a pin fastener pivotally journalled in the first end of the holding strap for removably securing the holder to a garment, and said aural stethoscope being attached to the holder so that the aural stethoscope can be coiled up and placed in the closed loop created when the holding strap is folded over on itself.

In yet another aspect of the present invention there is provided a device for holding articles for medical personnel, comprising a holding strap having a loop securing surface along its length thereof, the holding strap having a first end and a second end, a securing pad having a hook securing surface and an inner surface, the securing pad being attached to the first end of the holding strap with the inner surface contacting the loop securing surface of the holding strap so that when the holding strap is folded over on itself the loop securing surface at the second end and the hook securing surface of the securing pad mate to form a closed loop to hold the articles, and a pin fastener pivotally journalled between the holding strap and the securing pad for removably securing the device to a garment.

DESCRIPTION OF THE PREFERRED EMBODIMENTS

Figure 1:
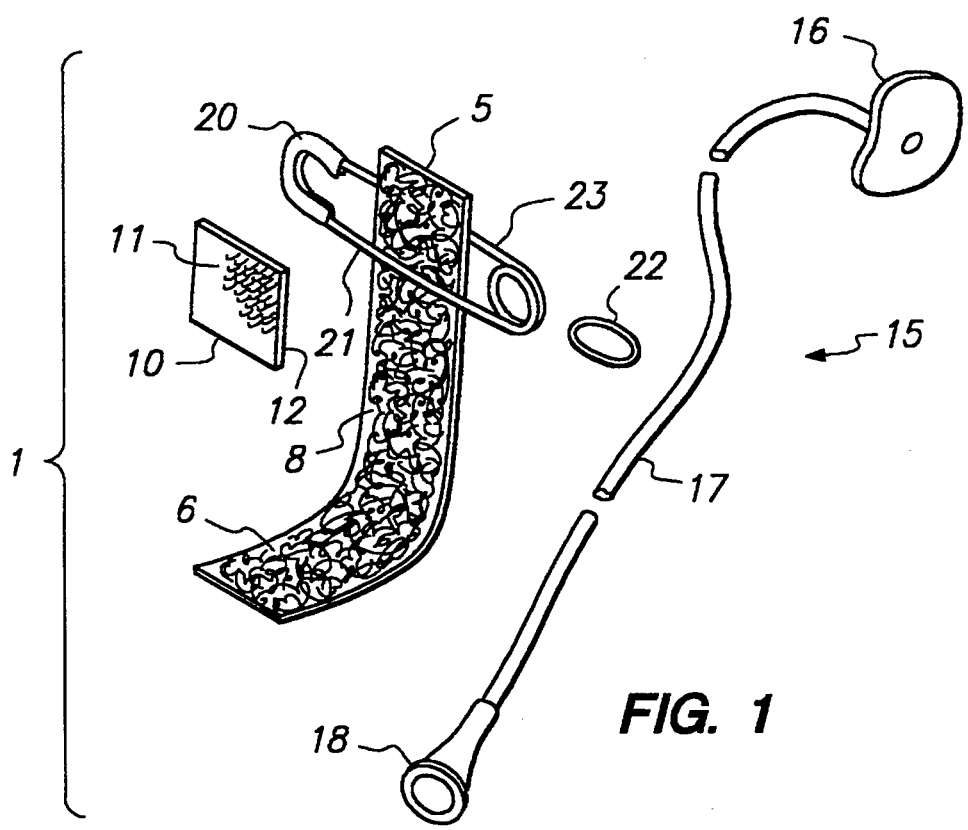
FIG. 1 is an exploded isometric view of a holder in accordance with the invention.

With reference to the drawing, FIG. 1 illustrates the construction of the holder in accordance with one embodiment of the invention. The holder, shown generally at 1, comprises holding strap 5, securing pad or patch 10, monaural stethoscope 15 and pin fastener 20.

The monaural stethoscope comprises a substantial length of tubing 17, earpiece 16, and connector 18. The tubing can have any desired diameter and thickness such as that of intravenous extension tubing or larger. For instance, the tubing can range from 0.375 to 0.625 inches (0.95 to 1.59 cm) in diameter. Likewise, the tubing can have various lengths such as in the range of 3 to 5 feet (0.9 to 1.5 meters). Earpiece 16 can be molded to fit in the outer ear, or have other forms such as a foam cylinder that is compressed and then placed in the outer ear canal and allowed to expand until it wedges itself in the outer ear canal. Connector 18 is used to connect the monaural stethoscope to a patient's precordial or esophageal stethoscope (not shown).

One side of holding strap 5 can include a loop securing surface 6 along some or all of the length thereof. Patch 10 can include a hook securing surface 11 on at least one side thereof. It is contemplated that part of the surface of the holding strap 5 may be free of the loop fasteners. One example of a holding strap and patch material that is especially suitable for use in the manufacture of the device of this invention is commercially available in the form of woven nylon hook and loop fasteners sold under the trade name "VELCRO" (available from VELCRO U.S.A., Inc., New Jersey). Pin fastener 20 can comprise a safety pin. One example of a pin fastener that is especially suitable is a diaper safety pin because it is lockable, light weight, durable and rustproof.

Figure 3:
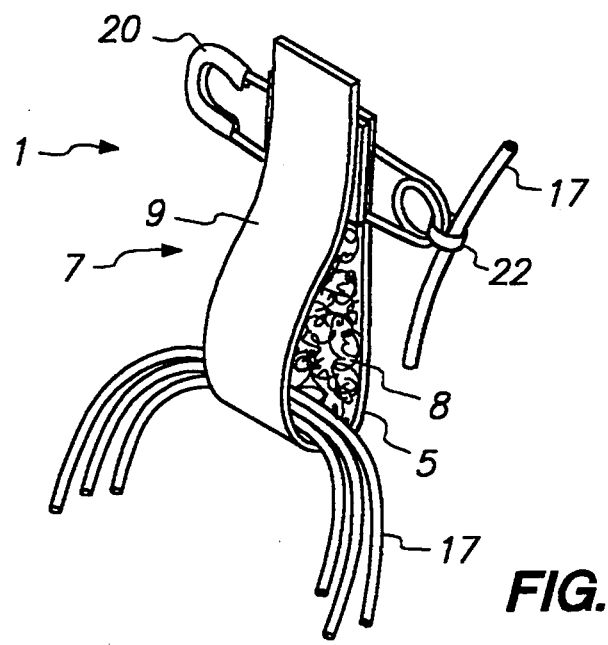
FIG. 3 is a front perspective view of the holder in the closed position.
Figure 4:
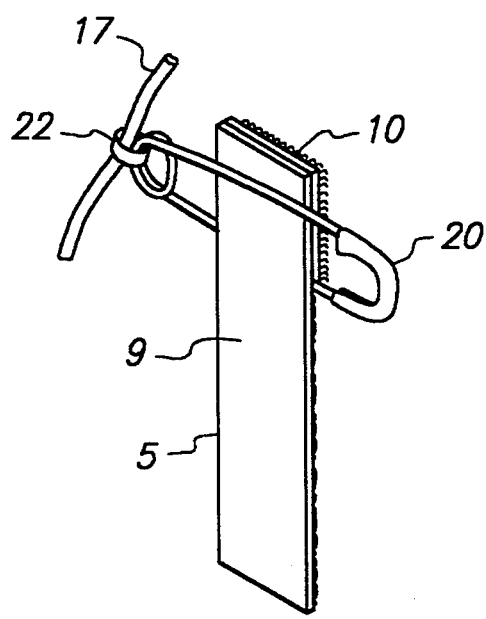
FIG. 4 is a rear perspective view of the holder in the open position.

To construct one embodiment of the present invention, holding strap 5 is placed between fixed arm 21 and movable arm 23 of the pin fastener 20, as shown in FIG. 3. In this case, movable arm 23 faces back side 9 of the holding strap 5, as shown in FIG. 4. Patch 10 is then placed over arm 21 and attached to strap 5 so that the arm 21 is held between front side 8 of holding strap 5 and back surface 12 of patch 10. With this arrangement, patch 10 is secured over arm 21 so that the pin fastener 20 is allowed to pivot around arm 21. In this way, the holder is free to pivot about an axis through arm 21 that is essentially parallel to the chest of the user, thus allowing freedom of movement of the holder away from the body of the user. Patch 10 may be secured to holding strap 10 by a variety of means such as stapling, sewing, gluing, etc. as long as the pin fastener is allowed to pivot around arm 21. However, it is also contemplated that the pin fastener may be held in a manner such that it does not pivot.

In one embodiment, monaural stethoscope 15 is attached to one end of pin fastener 20 by tie 22. For instance, monaural stethoscope 15 can be attached to pin fastener 20 at a location along the tubing 17 such that there is a convenient length of tubing between the holder and the anesthesiologist's ear. Thus, the anesthesiologist can move his/her head freely without pulling the earpiece 16 from his/her ear. Tie 22 can comprise a variety of fasteners, such as a ratchet toothed bundling tie, a twist tie, etc. However, monaural stethoscope 15 may be attached directly to holding strap 5 or tubing 17 may be threaded through the coil spring loop of the pin fastener 20.

FIG. 3 shows tubing 17 of the monaural stethoscope in its coiled and retained position in holder 1. Only a portion of the tubing is shown for simplicity. When holding strap 5 is folded over on itself, loop securing surface 6 on front side 8 of holding strap 5 mates with hook securing surface 11 of patch 10. In this way, a closed loop 7 is formed by the holding strap 5. It is advantageous to have the loop securing surface 6 of holding strap 5 in contact with itself when the closed loop is formed and to have the relatively small patch of hook securing surface 11 compared to the length of the holding strap so that the anesthesiologist can easily unhook holding strap 5 from the relatively small patch 10 in order to use the monaural stethoscope.

Figure 2:
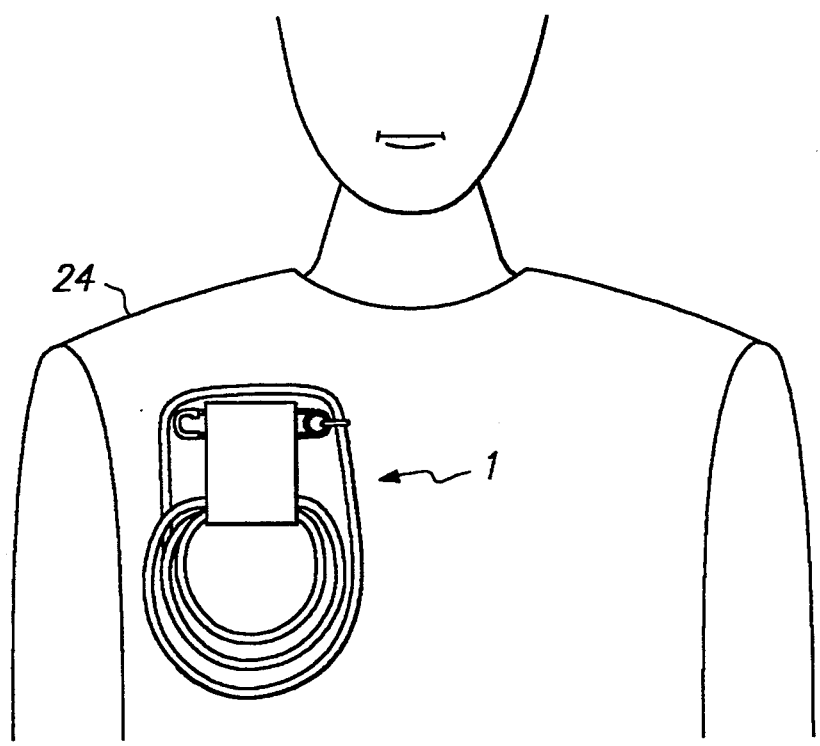
FIG. 2 is a front view of the upper torso area of a user with the holder of FIG. 1 attached to the garment of the user.

FIG. 2 shows holder 1 attached to the chest area of a medical garment with the monaural stethoscope in its coiled and retained position. With the present invention, the anesthesiologist can attach the holder and monaural stethoscope to a scrub suit at the beginning of the day with the pin fastener and have it readily available as he/she visits each patient. When the anesthesiologist is ready to administer anesthesia to a patient, he/she merely has to unhook holding strap 5 from patch 10, uncoil tubing 17, place earpiece 16 in his/her ear, and attach connector 18 to the patient's stethoscope. When the procedure is complete, the anesthesiologist disconnects connector 18, removes earpiece 16 from his/her ear or leaves it in his/her ear, coils tubing 17, places the tubing in holding strap 5, and mates loop securing surface 6 with hook securing surface 11 to retain tubing 17 conveniently until the anesthesiologist is ready to use the stethoscope again.

An added advantage is achieved by attaching tubing 17 to holder 1 by tie 22. For instance, when the anesthesiologist has the earpiece in his/her ear and connector 18 is connected to the patient's stethoscope, if the anesthesiologist moves too far away from the patient, the tubing will pull on the anesthesiologist's scrub shirt 24 via pin fastener 20 instead of pulling the earpiece out of his/her ear.

Figure 5:
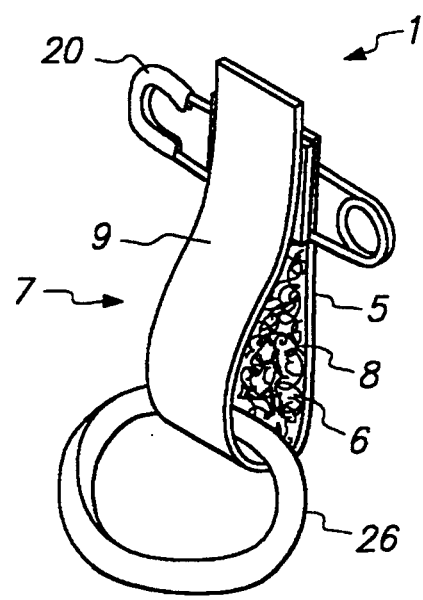
FIG. 5 is a front perspective view of the holder in the closed position for retaining an article such as a ring.

FIG. 5 shows holder 1 adapted to hold personal articles such as ring 26 for medical personnel. For instance, when medical personnel wash their hands for surgery, it is advantageous to use holder 1 to retain personal items such as rings, watches, key rings, etc. instead of putting them in the pockets of the scrub suit where they may inadvertently be lost when the garment is placed in the laundry.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A medical device, comprising:
   a holding strap having a loop securing surface;
   a patch having a hook securing surface, the patch being attached to a first end of the holding strap so that when the holding strap is folded over on itself the loop securing surface and hook securing surface mate to form a closed loop;

a pin fastener supported at the first end of the holding strap for removably securing the holding strap to a garment; and an aural stethoscope attached to the medical device so that tubing of the aural stethoscope can be coiled up and placed in the closed loop created when the holding strap is folded over on itself.

2. The medical device of claim 1 wherein the pin fastener is a safety pin.

3. The medical device of claim 1 wherein the aural stethoscope is attached to an end of the pin fastener.

4. The medical device of claim 1 wherein the loop securing surface extends substantially along the entire length of the holding strap.

5. The medical device of claim 1 wherein the pin fastener is pivotally journalled to the first end of the holding strap.

6. A holder for an aural stethoscope or the like, comprising:

a holding strap having a loop securing surface along a length thereof;

a patch having a hook securing surface, the patch being attached to a first end of the holding strap so that when the holding strap is folded over on itself the loop securing surface and hook securing surface mate to form a closed loop in which the aural stethoscope can be held; and a pin fastener pivotally journalled to the first end of the holding strap for removably securing the holder to a garment.

7. The holder of claim 6 wherein the pin fastener is a safety pin.

8. The holder of claim 6 wherein the aural stethoscope is attached to an end of the pin fastener.

9. A device for holding articles for medical personnel, comprising:

a holding strap having a loop securing surface along a length thereof, the holding strap having a first end and a second end;

a securing pad having a hook securing surface and an inner surface, the securing pad being attached to the first end of the holding strap with the inner surface contacting the loop securing surface of the holding strap so that when the holding strap is folded over on itself the loop securing surface at the second end and the hook securing surface of the securing pad mate to form a closed loop for holding the articles; and a pin fastener pivotally journalled between the holding strap and the securing pad for removably securing the device to a garment.

10. The device of claim 9 wherein the pin fastener is a safety pin.

11. The device of claim 9 wherein the securing pad includes a hook securing surface on the inner surface thereof, the pin fastener including a fixed arm and a movable arm, the fixed arm being held between the securing pad and the holding strap and the movable arm having a pointed free end for attaching the device to a garment.

* * * * *